Figure 1:
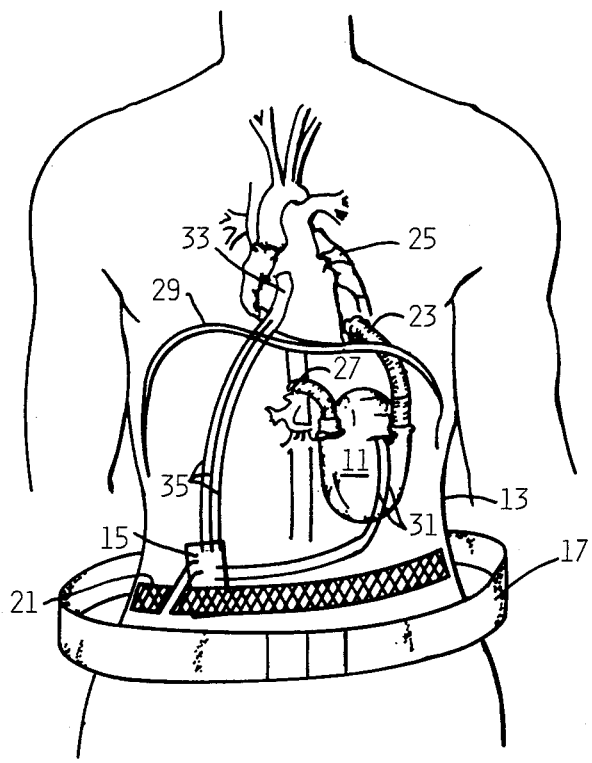

United States Patent [19]

Portner

[11] Patent Number: 4,666,443
[45] Date of Patent: May 19, 1987

[54] BIVENTRICULAR CIRCULATORY ASSIST SYSTEM AND METHOD

[75] Inventor: Peer M. Portner, Kensington, Calif.

[73] Assignee: Novacor Medical Corporation, Oakland, Calif.

[21] Appl. No.: 853,464

[22] Filed: Apr. 18, 1986

[51] Int. Cl.$^4$ ............................................... A61F 2/22
[52] U.S. Cl. ...................................... 623/3; 128/1 D; 128/DIG. 3
[58] Field of Search ............. 623/3; 128/1 D, DIG. 3

[56] References Cited

U.S. PATENT DOCUMENTS

| 4,143,661 | 3/1979 | LaForger et al. | 623/3 X |
|---|---|---|---|
| 4,152,786 | 5/1979 | Clark et al. | 623/3 |
| 4,384,829 | 5/1983 | Conley et al. | 623/3 X |
| 4,453,537 | 6/1984 | Spitzer | 623/3 X |
| 4,457,673 | 7/1984 | Conley et al. | 623/3 X |

OTHER PUBLICATIONS

Davis C. Drinkwater, Jr., et al., "Cardiac Assist and Myocardial Repair with Synchronously Skeletal Muscle", 1980; pp. 271–274.
Michael L. Dewar, et al., "Synchronously Stimulated Skeletal Muscle Graft for Myocardial Repair", Mar. 1984; pp. 325–331.
Ian R. Neilson, et al., "Left Ventricular Assistance in Dogs Using a Skeletal Muscle Powered Device for Diastolic Augmentation", May 1985.
Adrian Kantrowitz, "Functioning Autogenous Muscle Used Experimentally as an Auxiliary Ventricle", pp. 305–307.
Bert K. Kusserow, et al., "A Small Ventricle-Type Pump for Prolonged Perfusions: Construction and Initial Studies, Including Attempts to Power a Pump Biologically with Skeletal Muscle", 1964, pp. 74–78.
Eisule Kusaba, et al., "A Diaphragmatic Graft for Augmenting Left Ventricular Function: A Feasibility Study", 1973, pp. 251–257.
John A. Macoviak, et al., "Replacement of Ventricular Myocardium with Diaphragmatic Skeletal Muscle", 1981, pp. 519–527.

Primary Examiner—Ronald L. Frinks
Attorney, Agent, or Firm—Fitch, Even, Tabin & Flannery

[57] ABSTRACT

A biventricular circulatory support system for a human patient is described. A mechanical first pump for assuming at least a part of the pumping load of the patient's left ventricle is implanted in the patient. A second pump for assuming at least a part of the pumping load of the patient's right ventricle is also implanted. The second pump includes a surgically prepared skeletal muscle pedicle with nerves and blood supply substantially intact. The muscle pedicle is applied directly to the right ventrical or is applied to an artificial pump sac. Electrical signals are applied to the first and second pumps as appropriate to cause pumping action in a predetermined relationship.

11 Claims, 2 Drawing Figures

BIVENTRICULAR CIRCULATORY ASSIST SYSTEM AND METHOD

This invention relates generally to circulatory support systems. More particularly, the invention relates to a totally implantable circulatory support system which combines the technologies of left ventricular assist pumping for augmenting systemic circulation and skeletal muscle pedicle stimulation for augmenting pulmonary circulation.

Various types of prosthetic devices which may be implanted in patients to provide or assist cardiac function are well known. Total heart implants, designed to completely replace a surgically removed heart, have been employed with some success and widely publicized.

A problem with respect to current implanted devices which totally replace the heart is that the power requirements of such devices and the limited volume of the thoracic cavity make it impractical or impossible to provide totally implantable power support for the device. Accordingly, transcutaneous pneumatic power lines have typically been employed for operating such devices. The necessity for the patient to remain tethered to a relatively large external device, together with the problems attendant to permanent transcutaneous power lines, lend significant undesirable attributes to the employment of devices of this type.

Since the left ventricle of the human heart typically supports about 85% of the total heart pumping load, it has been proposed to utilize a device which is limited to supporting left ventricular function. One type of such a device is shown and described in U.S. Pat. No. 4,457,673, issued July 3, 1984 and assigned to the assignee of the present invention. The pump described in the foregoing patent is implanted in a patient in the abdominal cavity and is connected such that, upon contraction or systole of the left ventricle, it receives blood therefrom and thereby fills. Upon cessation of systole, the pump contracts to expel its contents into the arterial system of the patient. As such, the pump takes over the load of the ventricle from which it receives blood, either partially or completely, thereby relieving the ventricle.

A major advantage of the type of pump just described is in its relatively low power requirements. Thus, the device is powered through a totally implantable power supply containing rechargeable batteries, which can be recharged by power transmitted transcutaneously through a so-called belt-skin transformer system. Such a system is described in U.S. Pat. No. 4,143,661, assigned to the assignee of the present invention.

Although the left ventricular assist system approach described above has been successful in assuming up to the full load imposed on the left ventricle, the right ventricle remains only indirectly assisted (only under circumstances of normal pulmonary ventricular resistance). This may be satisfactory in situations in which the right ventricle is not significantly impaired. However, where right ventricular function is significantly impaired along with the left ventricle function, the installation of a similar assist system for the right ventricle is very difficult or impossible due to limitations in body cavity volume.

It is an object of the present invention to provide an improved circulatory support system which is biventricular, namely, capable of supporting the load for both left and right ventricles of a human patient.

Another object of the invention is to provide an improved biventricular circulatory support system which may be driven from a fully implantable power supply system.

Another object of the invention is to provide an improved method for biventricular circulatory support.

Figure 2:
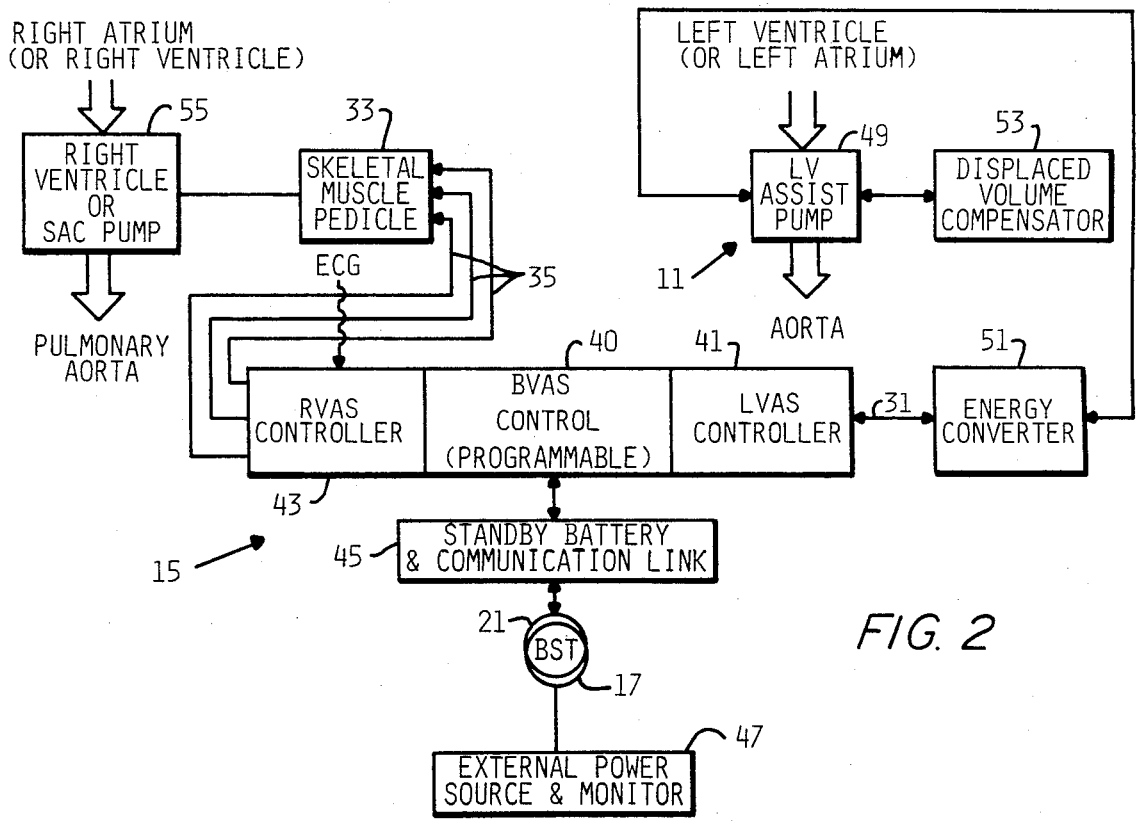

Other objects of the invention will become apparent to those skilled in the art from the following description, taken in connection with the accompanying drawings wherein:

FIG. 1 is a diagrammatic depiction of a biventricular circulatory assist system as implanted within a human patient and FIG. 2 is a block schematic diagram of the system of FIG. 1.

Very generally, the biventricular circulatory support system of the invention includes first pumping means for assuming at least a part of the pumping load of the patient's left ventricle. The first pumping means is connected between the left ventricle and the arterial (systemic) circulation of the patient and is responsive to electrical signals applied thereto to contract and pump blood. A second pumping means for assuming at least a part of the pumping load of the patient's right ventricle is also implanted. The second pumping means includes a surgically prepared skeletal muscle pedicle with nerves and blood supply intact and is placed on the right ventricle itself or around a pump sac of suitable material and configuration. The muscle pedicle is responsive to electrical signals applied thereto to contract and cause the second pump to pump. A control system applies electrical signals to each of the first and second pumping means in a predetermined relationship.

Referring now more particularly to FIG. 1, a blood pump in the form of a left ventricular assist device 11 is depicted implanted within the body 13 of a patient. The device is preferably of the type shown and described in U.S. Pat. Nos. 4,457,673 and 4,384,829. The system also includes an implanted module 15 that includes electronic power shaping and control components and a standby storage battery.

The system is powered and charged via a belt skin transformer (BST) having a primary coil which is constituted by an outer stretchy, body-conforming belt 17. A secondary, also stretchy, coil 21 is implanted subcutaneously about the waist. The primary coil 17 overlaps the secondary coil 21 and, when positioned about the waist of a wearer, is inductively coupled to the secondary coil 21. Because of the relatively large diameter of the two air core coils, a very high magnetic coupling coefficient is achieved in an overall light-weight iron-free system.

The belt skin transformer with its associated implanted and external power supplies, controllers, and other components is not shown in greater detail in FIG. 1. Such transformer and other elements, however, may be constructed in accordance with those described in U.S. Pat. No. 4,143,661 and U.S. patent application Ser. No. 757,786, filed July 22, 1985. In addition to providing power, the transformer can be used to communicate data and reprogram internal elements.

The implanted module 15 provides multiple electrical connections to the left ventricular assist device 11, the connections being shown at 31. As may be seen in FIG. 1, the left ventricular assist device 11 contains a input conduit 23 which is connected to the left ventricle of the patient's heart, indicated generally at 25. An output conduit 27 extends from the device 11 and is connected to the patient's systemic circulation, such as by grafting onto the supraceliac aorta. Of course, the possible connecting arrangements will be apparent to those skilled in the art. The conduit 23 may be of any suitable construction such as a woven Dacron (TM) tube, properly protected from kinking or compression, which pierces the pericardial portion of the patient's diaphragm, indicated at 29. Actual connection of the conduit 23 to the left ventricle may be via a suitable cannula (not shown) inserted, via the apex, into the left ventricular cavity. The outflow conduit 27 is of a suitable material, such as woven Dacron TM, and may be connected to the aorta at different locations, such as the supraceliac axis (or other systemic artery) by anastomosis routine to vascular surgery.

In operation, the blood pump 11 fills during ventricular systole by offering low resistance to the outflow from the left ventricle through the inflow conduit 23. Synchronized with systole, at, before, or after termination thereof, the pump 11 begins an eject cycle in which it contracts to expel its contents through the outflow conduit 27 into the patient's circulatory system. Energization signals are provided to the device 11 from the module 15 through suitable electrical leads 31.

The present invention results from a recognition that certain surgical techniques may be employed to simultaneously augment the right or pulmonary circulatory function which do not occupy a significant volume in the thoracic cavity and yet which are fully controllable electrically so that synchronization with an electrically driven mechanical left ventricular assist system and operation from a common power module may be achieved. The surgical techniques which are employed are those described in the following publications which are made a part hereof by incorporation by reference:

Drinkwater, Jr., Davis C., et al., "Cardiac Assist and Myocardial Repair with Synchronously Stimulated Skeletal Muscle", *American College of Sugeons* 1980 *Surgical Forum*, Vol. XXXI, pp. 271–274.

Dewar, Michael L., et al., "Synchronously Stimulated Skeletal Muscle Graft for Myocadial Repair", *The Journal of Thoracic and Cardiovascular Surgery*", St. Louis, Vol. 87, No. 3, pp. 325–331, March 1984.

Neilson, Ian R., et al., "Left Ventricular Assistance in Dogs Using a Skeletal Muscle Powered Device for Diastolic Augmentation", *Heart Transplantation*, Volume IV, No. 3, pp. 343–347, May, 1985.

Kantrowitz, Adrian, "Functioning Autogenous Muscle Used Experimentally as an Auxiliary Ventricle", State University of New York College of Medicine and Maimonides Hospital, Brooklyn, NY, pp. 305–307.

Kusserow, Bert K., et al., "A Small Ventricle-Type Pump for Prolonged Perfusions: Construction and Initial Studies, Including Attempts to Power a Pump Biologically with Skeletal Muscle", *Trans. Amer. So. Artif. Int. Organs*, pp. 74–78, 1964.

Kusaba, Eisuke, et al., "A Diaphragmatic Graft for Augmenting Left Ventricular Function: A Feasibility Study", *Trans. Amer. Soc. Artif. Int. Organs*, Vol. XIX, pp. 251–257, 1973.

Macoviak, John A., et al., "Replacement of Ventricular Myocardium With Diaphragmatic Skeletal Muscle", *J. Thorac Cardiovasc. Surg.*, 81:519–527, 1981.

In particular, the surgical techniques employed involve the implantation of a surgically prepared skeletal muscle pedicle (for example taken from the Latissimus Dorsi or Rectus Abdominis muscle) with nerves and blood supply intact. The muscle pedicle may be used in either of two ways. It may be placed directly on the right ventricular epicardium to augment right ventricular contraction, or it may be placed around a valved sac-type pump interposed between the right atrium (or right ventricle) and the pulmonary artery to augment right-sided (pulmonary) flow. In either case, electrical pulses applied at suitable intervals to the muscle pedicle cause the muscle to contract and provide the augmented pumping function for the right ventricle. The muscle implant is shown schematically at 33, and is stimulated by the electrical leads 35.

In the event that the skeletal muscle pedicle is placed on the free wall of the right ventricle to provide direct augmentation of contraction (a procedure called cardiomyoplasty), the stimulation and timing of the muscle are preferably controlled by electrocardiogram (ECG) signals obtained by means of suitably placed epicardial electrodes (not shown). On the other hand, if the muscle pedicle is used to actuate an auxiliary right ventricular assist sac-type blood pump, stimulation pulse timing may be obtained either from the control module 15 or from sensed ECG signals.

Referring now to FIG. 2, a general block diagram of the system of the invention is shown. The control means or control device 15 may incorporate a biventricular assist system (BVAS) controller 40 which is suitably programmable to govern the relationship, timing and duration of electrical signals in both left and right sides of the system of the invention. A left ventricular control 41 as described in the previously mentioned U.S. patent is connected to the controller 40. In addition, a suitable right ventricular control 43 comprising a pulse-train generator is provided to provide a series of pulses to appropriate locations in the skeletal muscle pedicle implanted to control the right ventricular assist portion of the invention. As illustrated, the implanted power supplies to the controller 40 and both right and left assist 41 and 43 portions are powered by a standby battery 45 which is charged from an external power source and monitor 47 via a belt-skin transformer (BST) as described in the aforementioned patent and patent application. However, a system could be employed wherein the battery 45 serves only as a back up and the primary driving power at all times is derived directly from the external power source through the BST.

The left ventricle assist portion utilizes the device 11 to pump blood from the left ventricle (or left atrium) to the aorta. The device 11 includes a pump 49 and a suitable energy converter 51 to activate the pump. A suitable displaced volume compensator 53 may also be provided connected to the left ventricular pump for volume compensation. Such a device is shown and described in U.S. Pat. No. 4,152,786, assigned to the assignee of the present invention.

With respect to the right side assist portion of the system, as mentioned above, the right ventricle control unit provides actuating pulses to the skeletal muscle pedicle synchronized with detected ECG signals. The skeletal muscle pedicle contractions thereby affect either the right ventricle directly or the sac pump, designated at 55, causing blood to flow from the right atrium (or right ventricle) to the pulmonary artery.

Normally, control of the right ventricle and left ventricle assist portions of the system of the invention is responsive to the cardiac cycle and outputs from the right and left ventricles. In this respect, the system as described operates as a pair of demand pumps. Nevertheless, those skilled in the art will be able to appreciate other control modes within the scope of this invention. Although shown as connected to the left ventricle, it will be apparent that the input for the device 11 could be connected to the left atrium instead.

It may be seen, therefore, that the system of the invention provides an improved means for biventricular circulatory support. The system combines a mechanical type pump for left ventricular assist with a skeletal muscle powered assist for right ventricular action. The system is readily implantable within the normal adult human and is capable of being operated by a fully implanted control system.

Various modifications of the invention will become apparent to those skilled in the art from the foregoing description and accompanying drawings. Such modifications are intended to fall within the scope of the appended claims.

What is claimed is:

1. A biventricular circulatory support system for a human patient comprising, mechanical first pumping means having means for connection and for assuming at least a part of the pumping load of the patient's left ventricle and responsive to first electrical signals applied thereto, second pumping means for assuming at least a part of the pumping load of the patient's right ventricle, said second pumping means including a surgically prepared skeletal muscle pedicle with nerves and blood supply substantially intact connected at one end thereof and responsive to second electrical signals applied thereto to contract and cause said second pumping means to pump, and means for applying first electrical signals to said first pumping means and second electrical signals to said second pumping means, said first and second electrical signals being applied in a predetermined relationship corresponding to a desired pumping phase relationship.

2. A system according to claim 1 wherein said skeletal muscle pedicle is adapted to be surgically placed directly on the patient's right ventricular epicardium to augment right ventricular contraction.

3. A system according to claim 1 wherein said second pumping means include a valved sac-type pump adapted to be interposed between the patient's right atrium or right ventricle and the patient's pulmonary artery to augment right-sided pulmonary flow, and wherein said skeletal muscle pedicle is placed around said valved sac-type pump.

4. A system according to claim 1 wherein said first pumping means comprise a mechanically actuated sac-type pump.

5. A system according to claim 1 wherein said first pumping means includes means for connection between the left ventricle and the aorta of the patient.

6. A system according to claim 1 wherein said control means include a pulse train generator adapted to be implanted within the patient.

7. A system according to claim 1 wherein said control means include means for developing said second signals in response to detected ECG signals from the patient.

8. A system according to claim 1 wherein said control means apply said first and second electrical signals in accordance with demand from the patient's left side and right side respectively.

9. A method for supporting the circulatory system of a patient, comprising, implanting in the patient mechanical first pumping means for assuming at least a part of the pumping load of the patient's left ventricle, said first pumping means being responsive to first electrical signals applied thereto, implanting second pumping means for assuming at least a part of the pumping load of the patient's right ventricle, said second pumping means including a surgically prepared skeletal muscle pedicle with nerves and blood supply substantially intact and responsive to second electrical signals applied thereto to contract and cause said second pumping means to pump, and implanting control means for applying first electrical signals to said first pumping means and second electrical signals to said second pumping means in a predetermined relationship.

10. A method according to claim 9 wherein the second electrical signals are coordinated with the ECG signals of the patient.

11. A method according to claim 9 wherein the first pumping means are connected between the left ventricle and the aorta of the patient.

* * * * *